United States Patent
Dorsel et al.

(10) Patent No.: US 6,251,685 B1
(45) Date of Patent: Jun. 26, 2001

(54) READOUT METHOD FOR MOLECULAR BIOLOGICAL ELECTRONICALLY ADDRESSABLE ARRAYS

(75) Inventors: Andreas Nikolaus Dorsel, Menlo Park; Mel N. Kronick, Palo Alto; Gary B. Gordon, Saratoga, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/252,208

(22) Filed: Feb. 18, 1999

(51) Int. Cl.$^7$ ................................................. G01N 27/327
(52) U.S. Cl. .............................. 436/172; 422/52; 422/55; 422/68.1; 422/82.08; 422/186; 436/159; 436/180; 436/46
(58) Field of Search ........................ 422/68.1, 52, 82.05, 422/82.07, 82.11, 91, 107, 108, 186.15, 186.16, 99, 102; 436/172, 159, 180, 46

(56) References Cited

U.S. PATENT DOCUMENTS

| | | | |
|---|---|---|---|
| 5,631,734 | 5/1997 | Stern et al. | 356/317 |
| 5,632,957 | 5/1997 | Heller et al. | 422/68.1 |
| 5,653,939 | 8/1997 | Hollis et al. | 422/50 |
| 5,741,462 | 4/1998 | Nova et al. | 422/68.1 |
| 5,798,083 | 8/1998 | Massey et al. | 422/52 |
| 5,837,475 | 11/1998 | Dorsel et al. | 435/7.1 |
| 6,099,803 | * 8/2000 | Ackley et al. | 422/68.1 |

FOREIGN PATENT DOCUMENTS

9628538 * 9/1996 (WO).

* cited by examiner

*Primary Examiner*—Jill Warden
*Assistant Examiner*—Yelena Gakh

(57) ABSTRACT

A method for reading out data from microlocations of a microelectronic array involves activating multiple microlocations in parallel and simultaneously detecting the responses from the activated microlocations to determine concentrations of molecular biological material at each microlocation. In a preferred embodiment, the microelectronic array includes electronically addressable electrodes at each microlocation which can be individually activated via a control system. An electrochemiluminescent detection technique is used to detect the presence and determine the concentration of bound molecular biological material that is located at each microlocation. Electrochemiluminescent material is utilized because it gives off light when excited by an applied electrical field. With an addressable microelectronic array, electrical fields can be applied to various combinations of microlocations simultaneously to allow readout of several microlocations in parallel. This is in contrast to the laser-based readout approach which applies activation energy to one microlocation at a time by impacting each microlocation with a single laser system. Reading out multiple microlocations simultaneously in accordance with the invention can produce significant time savings in large arrays.

19 Claims, 8 Drawing Sheets

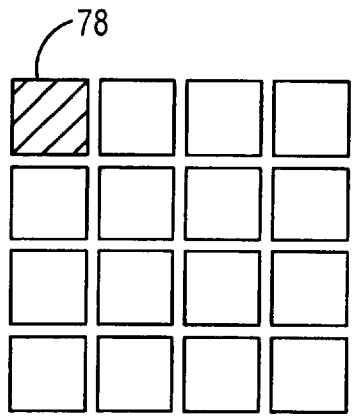
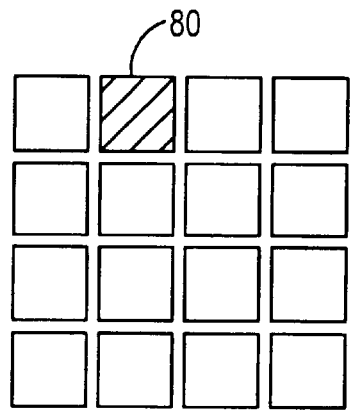
FIG. 3A  FIG. 3B
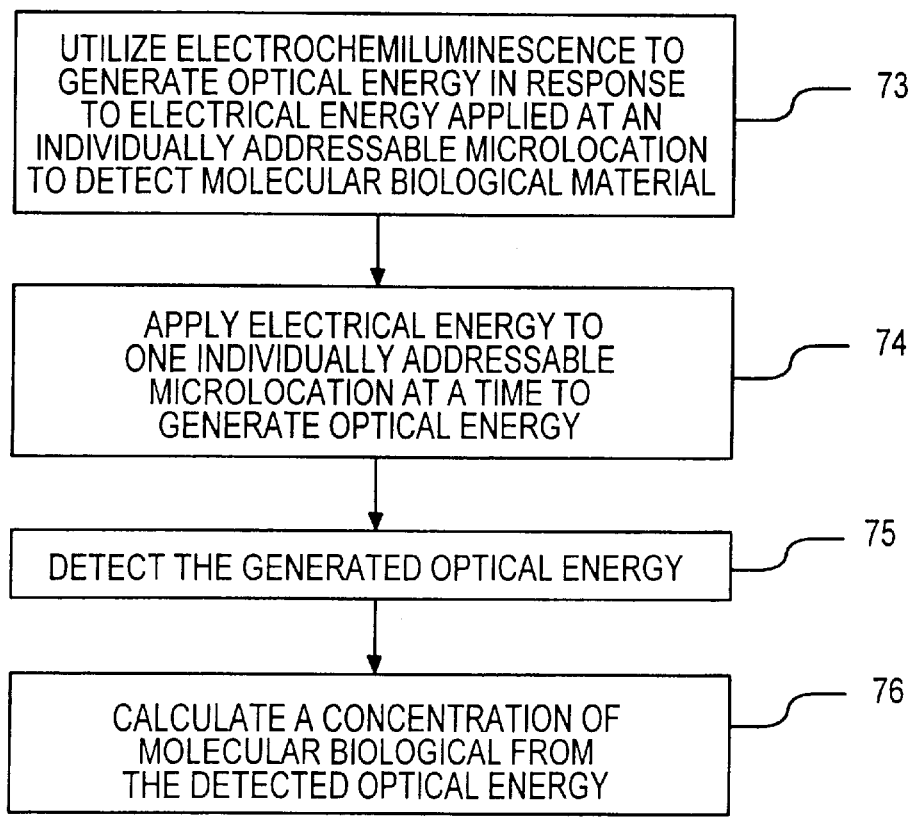
FIG. 4

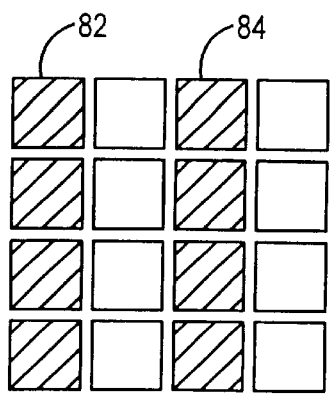
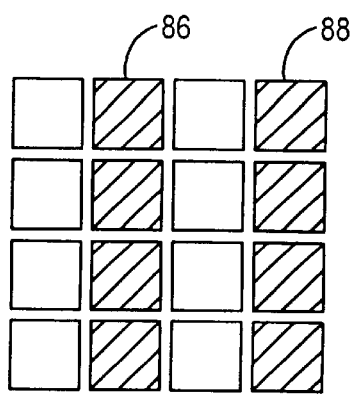
FIG. 5A               FIG. 5B
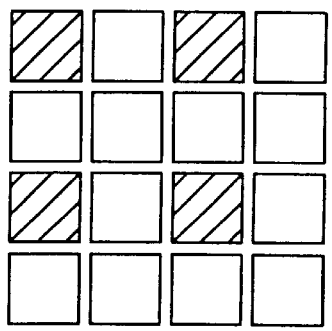
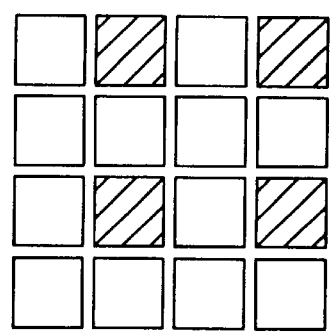
FIG. 6A               FIG. 6B
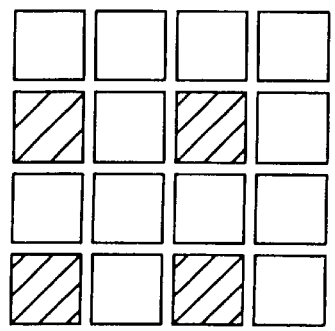
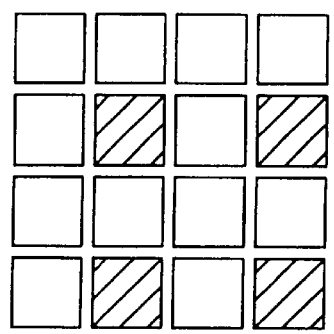
FIG. 6C               FIG. 6D

READOUT METHOD FOR MOLECULAR BIOLOGICAL ELECTRONICALLY ADDRESSABLE ARRAYS

TECHNICAL FIELD

The invention relates to microelectronic array systems for performing analysis of molecular biological material such as DNA and RNA. More particularly, the invention relates to methods and systems for reading out data from microelectronic array systems.

BACKGROUND ART

Microelectronic arrays having electronically addressable microlocations, or features, are being used to carry out in-parallel multiple sample DNA hybridization analysis on a source DNA sample. The microelectronic arrays are fabricated on semiconductor substrates using semiconductor processing techniques. An exemplary microelectronic array system for performing molecular biological diagnosis is disclosed in U.S. Pat. No. 5,632,957, entitled "Molecular Biological Diagnostic Systems Including Electrodes," issued to Heller et al. (hereinafter Heller). Microelectronic arrays such as Heller allow charged molecules to be actively moved and concentrated at designated microlocations within an array. In one application, DNA probes are located at specific microlocations and then target DNA molecules are electronically directed to specific probes in order to promote hybridization of the target DNA with the probe DNA. By utilizing electronically addressable microelectronic arrays to concentrate DNA, hybridization rates are significantly accelerated over prior passive hybridization techniques.

There are many techniques available for detecting the extent of DNA hybridization that has occurred on DNA arrays, whether microelectronic or not. A common technique involves incorporating fluorescent markers, or labels, into the target DNA that is provided to hybridize with the probe DNA. After hybridization, each microlocation can be contacted with light, for example laser light, in order to activate any fluorescent labels that are present at a particular microlocation. Fluorescent light given off from the fluorescent material located at the microlocations is measured and related to DNA concentrations.

In most detection techniques that require outside sources of energy, such as laser light energy, to activate a label, the activation energy is applied to the array one microlocation at a time. Specifically, in a laser-activated system, the laser systematically steps through each microlocation, or pixel, applying laser light to each location individually. Laser-based readout systems are disclosed in U.S. Pat. No. 5,631,734, entitled "Method and Apparatus for Detection of Fluorescently Labeled Materials," issued to Stern et al. and U.S. Pat. No. 5,653,939, entitled "Optical and Electrical Methods and Apparatus for Molecule Detection," issued to Hollis et al. Although sequentially reading out microlocations works well when the number of microlocations is small, when the number of microlocations in a microelectronic array is large, the readout time required to individually read each microlocation can be significant.

In view of the advancements involved with electrically addressable microelectronic arrays and in view of the limitations involved with sequentially activating microlocations on any DNA array with an outside source of energy such as laser light, what is needed is a readout method that takes advantage of the addressing control capability of microelectronic arrays in order to more efficiently read out desired biological data.

SUMMARY OF THE INVENTION

A method for reading out data from microlocations of a microelectronic array involves activating multiple microlocations in parallel and simultaneously detecting the responses from the activated microlocations to determine concentrations of molecular biological material at each microlocation. In a preferred embodiment, the microelectronic array includes electronically addressable electrodes at each microlocation which can be individually activated via a control system. An electrochemiluminescent detection technique is used to detect the presence and the concentration of hybridized molecular biological material that is located at each microlocation. Electrochemiluminescent material is utilized because it gives off light when in the presence of an electrical field. With an addressable microelectronic array, electrical fields can be applied to various combinations of microlocations simultaneously to allow readout of several microlocations in parallel. This is in contrast to the laser-based readout approach which applies activation energy sequentially to each microlocation by impacting each microlocation one after another with a single laser beam. Reading out multiple microlocations simultaneously in accordance with the invention can produce significant time savings in large arrays.

A preferred system for implementing the readout method of the invention includes a microelectronic array and a complementary detection system. The microelectronic array consists of multiple microlocations that are formed on a semiconductor substrate using integrated circuit fabrication technology. The microlocations are electronically addressable locations where manipulation of biological molecules occurs, such that each of the microlocations represents an area of defined, or constant, biological material. Preferably, the microlocations are configured in arrays of linear columns and rows, however, other configurations are possible. The number of microlocations in an array may be from 2 to about 16,000,000, preferably from about 100 to 100,000, and the size of each microlocation may be from 5 $\mu m^2$ to about 1 $mm^2$, usually about 100 $\mu m^2$ to about 200 $\mu m^2$. Each microlocation is individually connected to contact pads which enable the electronic array to be connected to control systems that can individually control the microlocations. In an alternative embodiment, each microlocation has leads that are connected to address decoders such that each microlocation does not have a dedicated contact pad requiring connection to a control system.

There are different known techniques available to manipulate and concentrate biological material at designated microlocations. The specific technique utilized is not critical to the invention.

A preferred detection system includes a detector that is located directly above, and in close proximity with, the microlocations of an array. The detection system may also include optics as needed to provide adequate light collection. In a preferred embodiment, the optics include an objective lens that captures light generated from the microlocations and directs the light to the detector. The detector may be a spatially resolving detector such as a CCD array or single-element detector such as a single photo cell. Optical filters and/or additional lenses may be placed between the first lens and the detector to further improve light detection.

The preferred readout method includes activating multiple microlocations in parallel to initiate an electrochemiluminescent reaction. Some techniques of activating multiple microlocations in parallel are more preferred than others. Two categories of parallel readout are referred to as partially parallel readout and fully parallel readout. Various preferred examples of partially parallel readout techniques are briefly described below in addition to a fully parallel readout technique. Preferably, activated microlocations are distributed such that light generated from the microlocations can be individually distinguished using a detection system that has only moderate spatial resolution. That is, adjacent activated microlocations should be separated by enough space on the array that a detection system with moderate resolution can distinguish the light being emitted from each microlocation. An example of a partially parallel readout technique involves activating alternating columns of microlocations simultaneously. Activating alternating columns of microlocations reduces interference (e.g., crosstalk) that could be encountered between adjacent columns of microlocations. If more space is needed between columns, then every $M^{th}$ column (where M>2) can be activated, instead of every other column. The column-by-column approach can be easily implemented as a row-by-row approach.

Another example of a partially parallel readout technique involves activating the microlocations at the intersection of alternating columns and rows such that no activated microlocations are directly adjacent to any other activated microlocations. As with the column-by-column approach, if alternating columns and alternating rows do not reduce signal interference enough, then microlocations can be activated at the intersection of every $M^{th}$ column and every $N^{th}$ row (where M>2 and N>2), with the columns and rows shifting in subsequent steps as needed to activate every microlocation. Activating microlocations in a partially parallel manner decreases detection time while reducing interference between microlocations.

The fully parallel readout technique preferably involves activating all of the microlocations simultaneously and detecting the generated light with a detection system having a high resolution CCD array. Preferably, a high resolution CCD array has pixels that are smaller than the microlocations. All of the microlocations are activated in parallel by simultaneously applying current/voltage to all of the electrodes to initiate an electrochemiluminescent reaction. With a high resolution CCD array and high numerical aperture optics, the light emitted from each microlocation can be individually distinguished and a specific biological concentration for each particular microlocation can be calculated. Simultaneously activating all microlocations for detection of molecular biological material enables rapid readout of a microelectronic array. The readout time for microlocations is becoming increasingly important as the number of microlocations in an array increases.

In an alternative embodiment of the invention, a sequential readout technique is utilized that involves activating each microlocation separately in a sequence and detecting the corresponding light that is generated as a result of the electrochemiluminescent reaction. The microlocations are individually activated by applying a driving voltage separately to each electronically addressable microlocation. A preferred detection system to utilize with the sequential readout technique has high light collection efficiency and poor spatial resolution. Because in the sequential readout technique only one microlocation is activated at a time, the detector does not need to distinguish spatial distribution of light. The sequential readout technique is similar to readout techniques that require laser light to impact each microlocation, but different from the laser based techniques in that electrochemiluminescent material at the microlocations is being activated via the individually addressable electrodes that are present in the array.

An advantage of the invention is that by utilizing electrochemiluminescence in an addressable array, multiple microlocations can be read out simultaneously, thereby reducing readout time. In addition, with partially parallel readout, light interference between microlocations is controlled such that lower resolution detection systems provide acceptable readout performance, while providing significant readout time savings when compared to a purely sequential readout.

BRIEF DESCRIPTION OF THE DRAWINGS

FIGS. 3A and 3B are examples of the sequential readout technique in accordance with the invention.

FIG. 4 is a process flow diagram of a sequential readout method in accordance with the invention.

FIGS. 5A and 5B are examples of the partially parallel readout technique in accordance with the invention.

FIGS. 6A through 6D are examples of the partially parallel readout technique in accordance with the invention.

DETAILED DESCRIPTION

Figure 1:
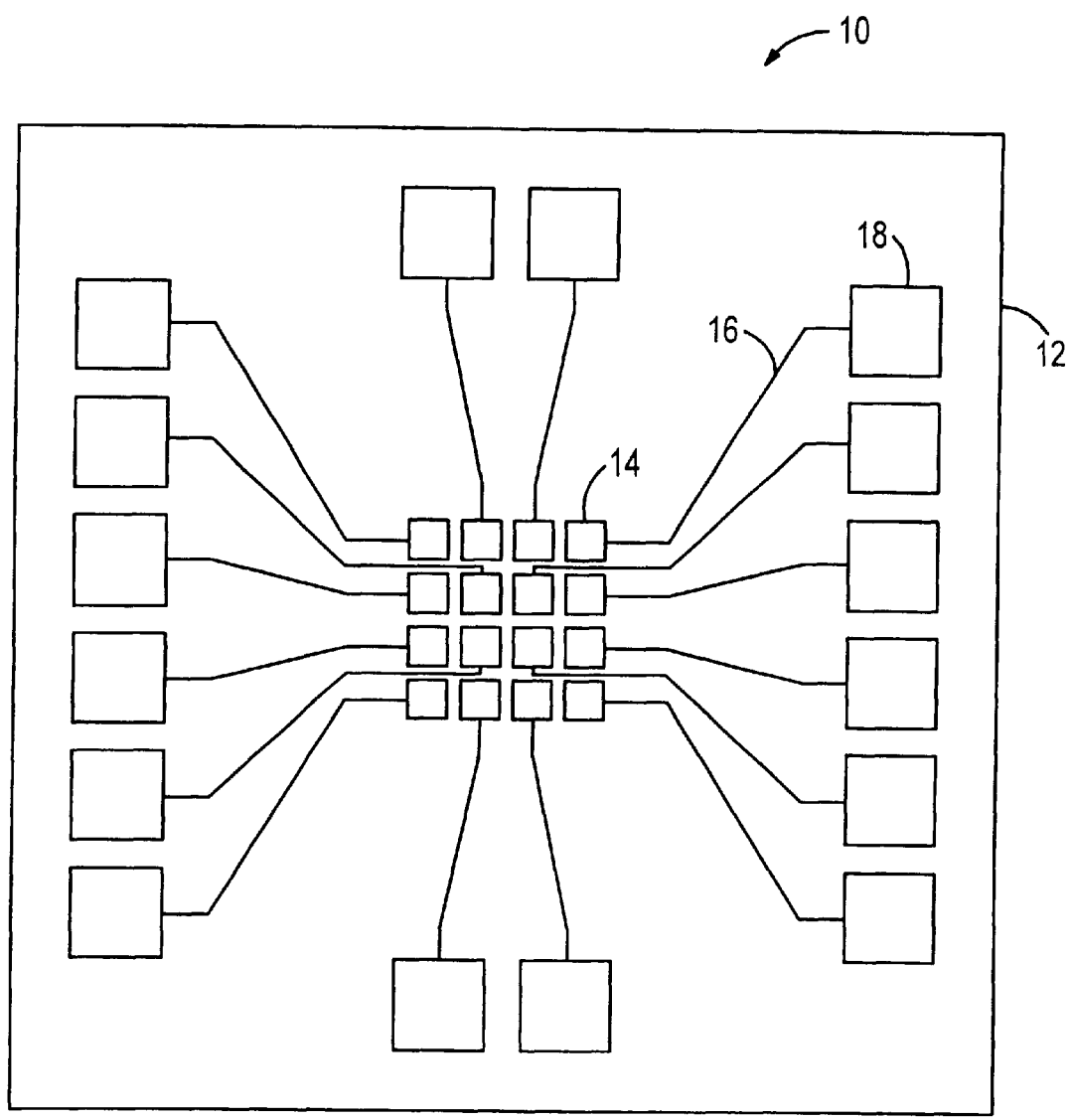
FIG. 1 is a depiction of a microelectronic array having sixteen microlocations in accordance with the prior art.

FIG. 1 is a depiction of a microelectronic array that is utilized with the readout techniques that are the focus of the invention. It should be noted that other microelectronic arrays and techniques for biological material manipulation can be utilized with the inventive readout techniques described herein. The following array is described for example purposes. Referring to FIG. 1, a microelectronic array 10 consists of multiple microlocations that are formed on a semiconductor substrate 12 using integrated circuit fabrication technology. The microlocations are the electronically addressable locations where hybridization or binding of biological molecules takes place. Preferably, the microlocations are configured in arrays of linear columns and rows, however other configurations are possible. Although an array of sixteen microlocations is shown in FIG. 1 for description purposes, a preferred microelectronic array will have more microlocations, for example, the number of microlocations may be from 2 to about 16,000,000, preferably from about 100 to 100,000. The size of each microlocation may be from 5 $\mu m^2$ to about 1 $mm^2$, usually about 20 $\mu m^2$ to about 200 $\mu m^2$.

As shown in FIG. 1, each microlocation 14 is individually connected by a lead 16 to a contact pad 18. The contact pads enable the microelectronic array to be connected to control systems (not shown) that allow the microlocations to be individually addressable. Although contact pads are shown, other IC packaging techniques can be used.

Using the array, biological material is manipulated to accomplish desired movement and/or transformation. After the material is manipulated, it is necessary to measure the concentrations of biological material at the microlocations. In the preferred embodiment, known electrochemiluminescent (ECL) techniques are used to detect the presence of molecular biological material at the microlocations. Electrochemiluminescence is a process in which light is generated when a low voltage is applied to an electrode and as a result a cyclical oxidation-reduction reaction of a ruthenium metal ion is triggered. Known ECL techniques are described by Richard O. Williams, "Electrochemiluminescence: A New Assay Technology," *IVD Technology*, November 1995, and by Gary F. Blackburn et al., "Electrochemiluminescence Detection for Development of Immunoassays and DNA Probe Assays for Clinical Diagnosis," Clinical Chemistry, Vol. 37, No. 9, 1991, which are both incorporated by reference.

Example patents describing ECL techniques include EPO 877252, EPO 871864, U.S. Pat. No. 5,811,236 and U.S. Pat. No. 5,770,459. The ECL detection technique generally involves labeling, or marking, target molecules with ECL material. The ECL material generates light when a low voltage electrical field is present. As a result, when target molecules, marked with ECL material, hybridize with probe material at individual microlocations, the ECL material is brought into close proximity with the electrodes at the microlocations. A voltage can then be applied to an electrode, causing light to be generated in proportion to the concentration of ECL material (and therefore target biological material) present at the microlocation. A light detection system placed in close proximity to the microelectronic array is utilized to detect generated light. While intensity of generated light is used to quantify biological concentration, other characteristics of the generated light, such as wavelength, may be used to identify other attributes, such as mere presence, of the molecular biological material.

The ECL detection techniques are utilized because detection can be triggered by electrically exciting ECL material at microlocations via the individually addressable leads, instead of optically activating fluorescent material at microlocations via a laser beam. In addition, activating microlocations in an electronically addressable system reduces mechanical system requirements and increases flexibility. Using an appropriate array of electrodes, the readout techniques described below could be used with ECL material even on arrays that are not synthesized using electronic addressing.

Figure 2:
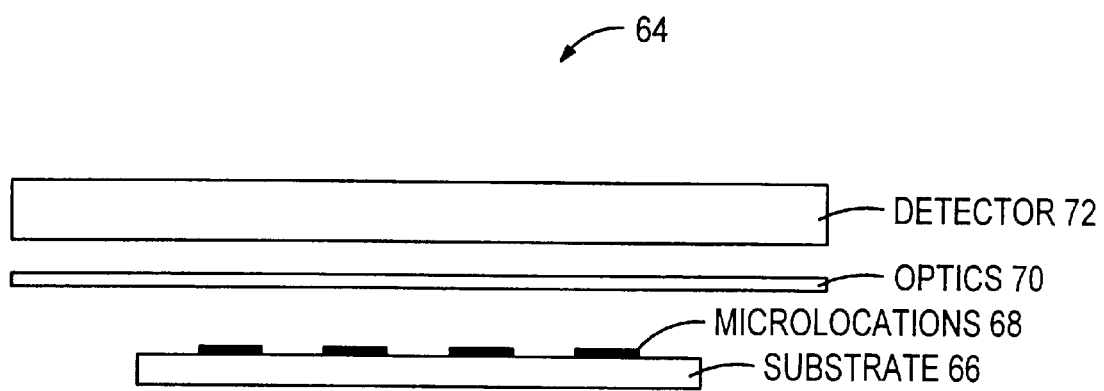
FIG. 2 is a depiction of a preferred detection system shown in relation to the substrate and microlocations of a microelectronic array.

FIG. 2 is a depiction of an example detection system 64 shown in relation to the substrate 66 and microlocations 68 of a microelectronic array. As can be seen, the detection system may include optics 70 and a detector 72. In a preferred embodiment, the optics include an objective lens that captures light generated from the microlocations and directs the light to the detector. In an alternative embodiment, optical filters and/or additional lenses can be placed between the first lens and the detector to further manipulate the generated light for improved detection. The detector may include a multi-dimension resolving detector such as a CCD array or a one-dimension resolving detector such as a single photo cell. Depending on the detector utilized, optics may not be necessary. It should be noted that FIG. 2 is not to scale and in a preferred embodiment the individual microlocations would be much smaller relative to the optics and the detector.

As will be described in further detail below, the type of detection system utilized with a microelectronic array is dependent on the readout technique used. In one readout technique, the detection system has high light collection efficiency and poor spatial resolution (imaging quality). Although the detection system has poor spatial resolution, the detection system can sense light generated from any point on the microelectronic array. A detection system of this type can be made to detect small amounts of light, but is not good at distinguishing the location of the source of the light. In another embodiment, the detection system has lower light collection efficiency but high spatial resolution. In addition, the detection system may have a high numerical aperture (NA) in order to provide a wide range of light detection. A conventional CCD array is preferable in this embodiment. In another alternative embodiment, a third detection system has lower light collection efficiency and moderate spatial resolution as well as a high numerical aperture. A major tradeoff between detection systems is that high resolution systems typically have higher initial purchase cost. The term "resolution" is used to designate performance that is adequate for separation of signals from different microlocations.

As stated above, the focus of the invention is the readout of data from the microelectronic arrays utilizing electrochemiluminescence. Three readout techniques referred to as sequential readout, partially parallel readout, and fully parallel readout are described below. All three readout techniques are preferably implemented with microelectronic arrays and detection systems as generally described with reference to FIGS. 1 and 2, although the readout techniques may be implemented with other array and detection systems.

The sequential readout technique involves activating each microlocation separately in a sequence and detecting the corresponding light that is generated as a result of an electrochemiluminescent reaction. The microlocations are individually activated by applying a driving voltage separately to each electronically addressable microlocation. FIG. 3A shows a first microlocation 78 being activated and FIG. 3B shows a second microlocation 80 being activated. Each microlocation is individually activated until the entire array is complete. A preferred detection system to be utilized with the sequential readout technique has high light collection efficiency and poor spatial resolution. As described above, the detector is able to detect small amounts of generated light, however the detector is not good at determining the spatial distribution of light. Because in the sequential readout technique only one microlocation is activated at a time, the detector does not need to distinguish spatial distribution of light.

In operation, the activation of microlocations is correlated with the detection of light in order to determine the concentration of biological material at each microlocation. The sequential readout technique is similar to readout techniques that require laser light to impact each microlocation, but different from the laser-based techniques in that ECL material at the microlocations is being excited via individually addressable electrodes. In the sequential readout technique, the amount of time spent analyzing each microlocation can be adjusted based on individual need. Although ECL detection techniques are preferred, other detection techniques may be utilized.

FIG. 4 is a process flow diagram for a preferred sequential readout technique in accordance with the invention. In a first step 73, electrochemiluminescence is utilized to generate optical energy in response to electrical energy applied at individually addressable microlocations to detect molecular biological material. In a step 74, electrical energy is applied to one individually addressable microlocation at a time to generate optical energy. In a step 75, the generated optical energy is detected. In a step 76, a concentration of molecular biological material is calculated from the detected optical energy.

The partially parallel readout technique involves activating at least two microlocations in parallel (i.e., simultaneously). The microlocations are activated in parallel by simultaneously applying a driving voltage to the desired individually addressable electrodes. Because the electrodes are individually addressable, many different combinations of microlocations can be activated in parallel. Preferably, activated microlocations are distributed such that light generated from the microlocations can be detected and individually distinguished with a detection system that has only moderate spatial resolution. That is, the activated microlocations should be separated by enough space that a detection system with moderate resolution can distinguish the light being emitted from each microlocation. Because multiple microlocations are read out at the same time, partially parallel readout exhibits significant time savings over sequential readout techniques. Some partially parallel readout combinations are described below for example purposes, however the examples are not intended to limit the possible combinations.

An example of a partially parallel readout technique is depicted in FIGS. 5A and 5B. In the readout technique, alternating columns of microlocations are activated simultaneously. Activating alternating columns of microlocations reduces interference that could be encountered between adjacent columns of microlocations. In the example, the microlocations of columns one 82 and three 84 are activated (FIG. 5A) and subsequently the microlocations of columns two 86 and four 88 are activated (FIG. 5B). Although in this example alternating columns are activated, in a variation of this example, every $M^{th}$ column could be activated, where M is greater than 2. After all of the $M^{th}$ columns are activated, the activated columns are shifted by one column and so on until all columns are activated. The column-by-column approach can be easily implemented as a row-by-row approach with all of the same variations.

Another example of a partially parallel readout technique is depicted in FIGS. 6A through 6D. In this approach, microlocations at the intersection of every other column and every other row are activated in a four-step readout process. In the first step shown in FIG. 6A, microlocations at the intersection of the first and third columns and the first and third rows are activated. In the second step, shown in FIG. 6B, microlocations at the intersections of the second and fourth columns and the first and third rows are activated. In the third step, shown in FIG. 6C, microlocations at the intersection of the first and third columns and the second and fourth rows are activated. In the fourth step, shown in FIG. 6D, microlocations at the intersection of the second and fourth columns and the second and fourth rows are activated. Distributing activated microlocations according to FIGS. 6A through 6D reduces interference between both adjacent rows and adjacent columns of microlocations that could be encountered while using readout techniques that involve simultaneously activating adjacent microlocations. An approach as shown in FIGS. 6A through 6D works well with microlocations that are addressable on a column and row basis similar to random access memory cells. In a variation of this approach, columns can be activated every $M^{th}$ column and/or the rows can be activated every $N^{th}$ row, with M and/or N being greater than 2. The activation based on the columns and rows is shifted in subsequent steps as needed to eventually activate every microlocation. Activating microlocations in a partially parallel manner decreases detection time while reducing interference between microlocations. Although specific partially parallel detection patterns are described with reference to FIGS. 5 and 6, other patterns which involve partially parallel readout are available. For example, microlocations can be read-out in a staggered column and row pattern.

Figure 7:
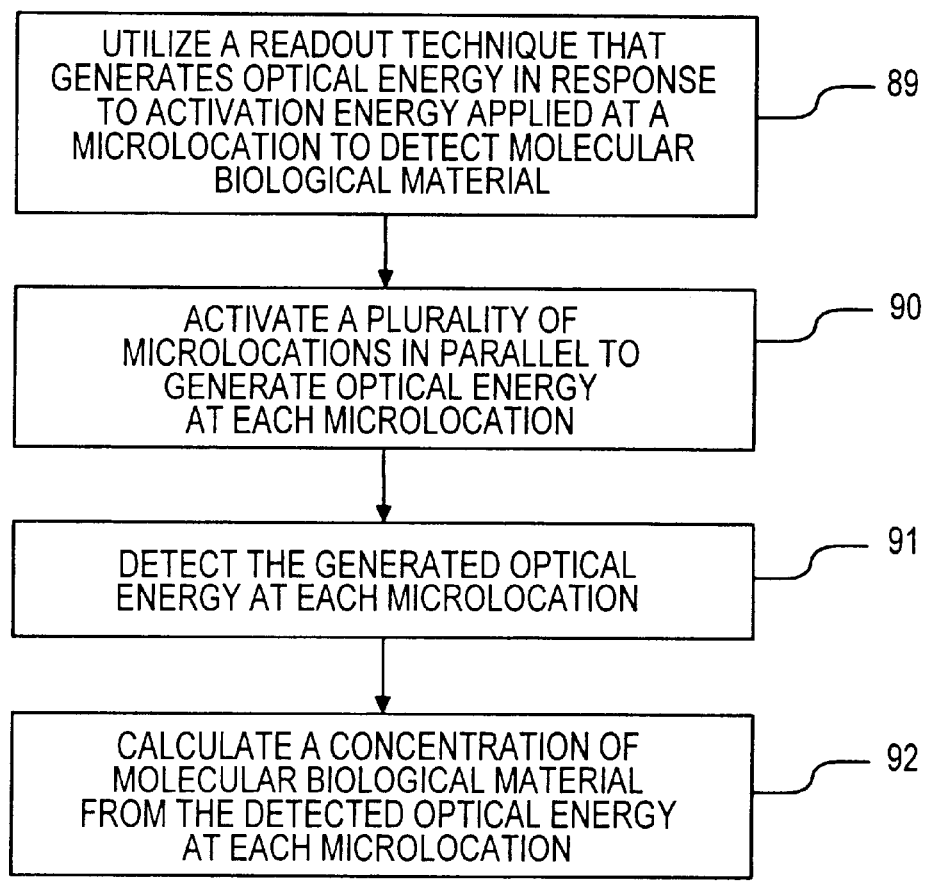
FIG. 7 is a process flow diagram of a partially parallel readout method in accordance with the invention.

FIG. 7 is a process flow diagram for a partially parallel readout technique in accordance with the invention. In a step 89, a readout technique that generates optical energy in response to activation energy applied at a microlocation is utilized to detected molecular biological material. In a step 90, a plurality of microlocations is activated in parallel to generate optical energy at each microlocation. In a step 91, the generated optical energy is detected at each microlocation. In a step 92, a concentration of molecular biological material is calculated from the detected optical energy at each microlocation.

Figure 8:
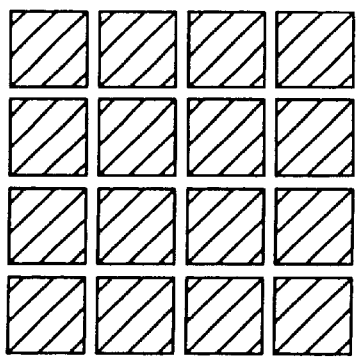
FIG. 8 is an example of the fully parallel readout technique in accordance with the invention.

The fully parallel readout technique involves activating all of the microlocations simultaneously and detecting the generated light with a detection system having a high resolution CCD array and optionally high numerical aperture optics. All of the microlocations are activated in parallel as shown in FIG. 8 by simultaneously applying a driving voltage to all of the electrodes. With a high resolution CCD array, the light emitted from each microlocation can be individually distinguished and a specific biological concentration for each particular microlocation can be calculated. Simultaneously activating all microlocations for detection of biological material provides for rapid readout from a microelectronic array, with readout time becoming especially important as the number of microlocations in an array increases. Specifically, fully parallel readout provides significant time savings over both the sequential and partially parallel readout techniques.

Any of the above readout techniques can be performed with a mirror located behind the biological material to enhance light collection efficiency. A mirror can be fabricated as part of the microelectronic array production process prior to synthesizing probe DNA.

In another alternative, a readout of all microlocations is initially performed using any of the readout techniques described above. The microlocations that have low signal-to-noise ratios can then be re-read for an additional period of time in a subsequent readout. To improve readout performance, the detection limit can be lowered by selectively integrating signals from the weakest microlocations for the longest time periods. This process of selectively adjusting readout times can even be advantageous with fully parallel readout because during the subsequent readout, microlocations with strong signals can be controlled to reduce interference with adjacent microlocations with weaker signals.

Figure 9:
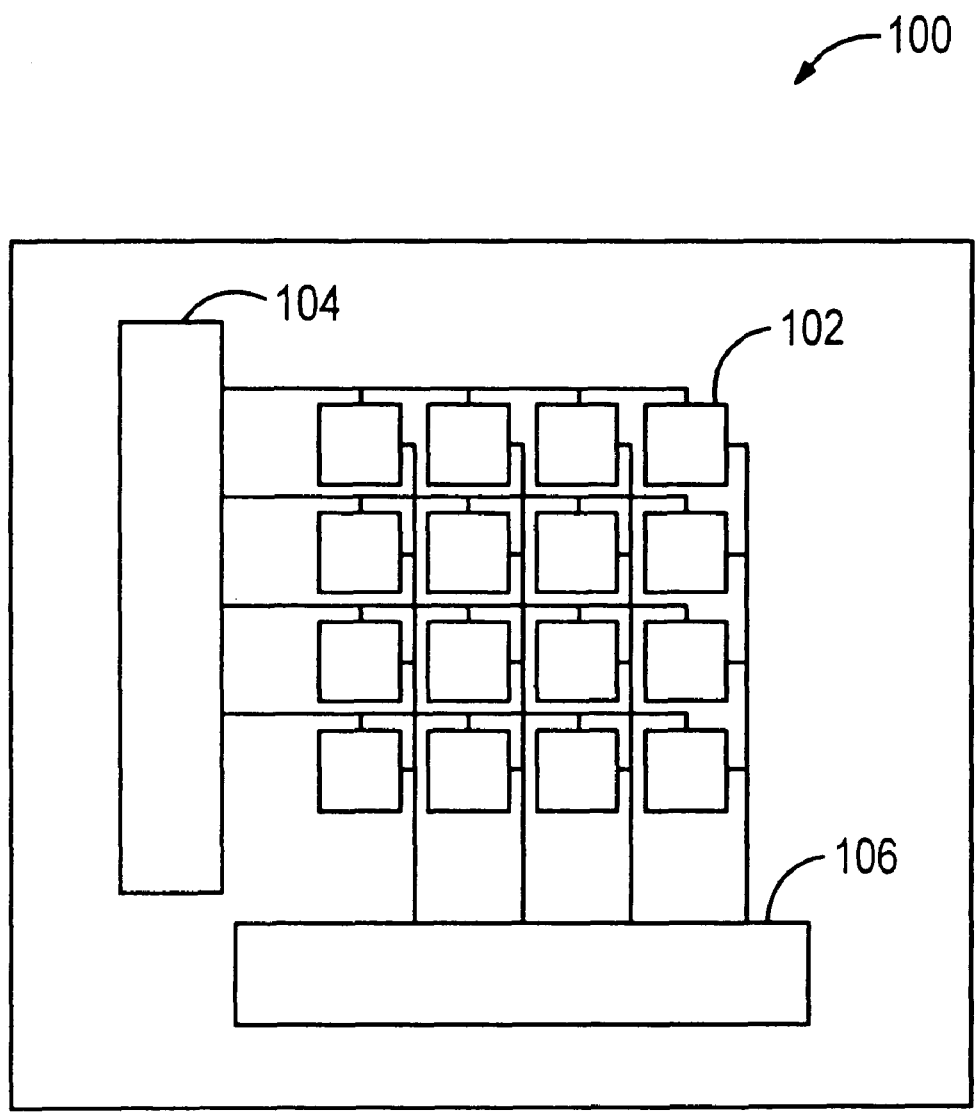
FIG. 9 is a depiction of a microelectronic array having X-axis and Y-axis address decoders in accordance with the invention.

Although the three readout techniques have been described with reference to known microelectronic arrays, the readout techniques can similarly be applied to a microelectronic array as disclosed in U.S. patent application Ser. No. 09/100,152, which is assigned to the assignee of the present invention. FIG. 9 is a depiction of the microelectronic array 100 having microlocations 102 that are individually addressable via on-chip address decoders 104 and 106. Having microlocations addressable via on-chip address decoders greatly reduces the number of connections required between the array and support systems, especially when large arrays are involved. For example, an array of 128×128 microlocations has a total of 16,384 microlocations. To control each microlocation with a dedicated connection would require 16,384 separate connections to a support system, which is impractical for the intended use of the microelectronic array. In a preferred system, a 14-line address bus can provide addressing for 16,384 microlocations.

Figure 10:
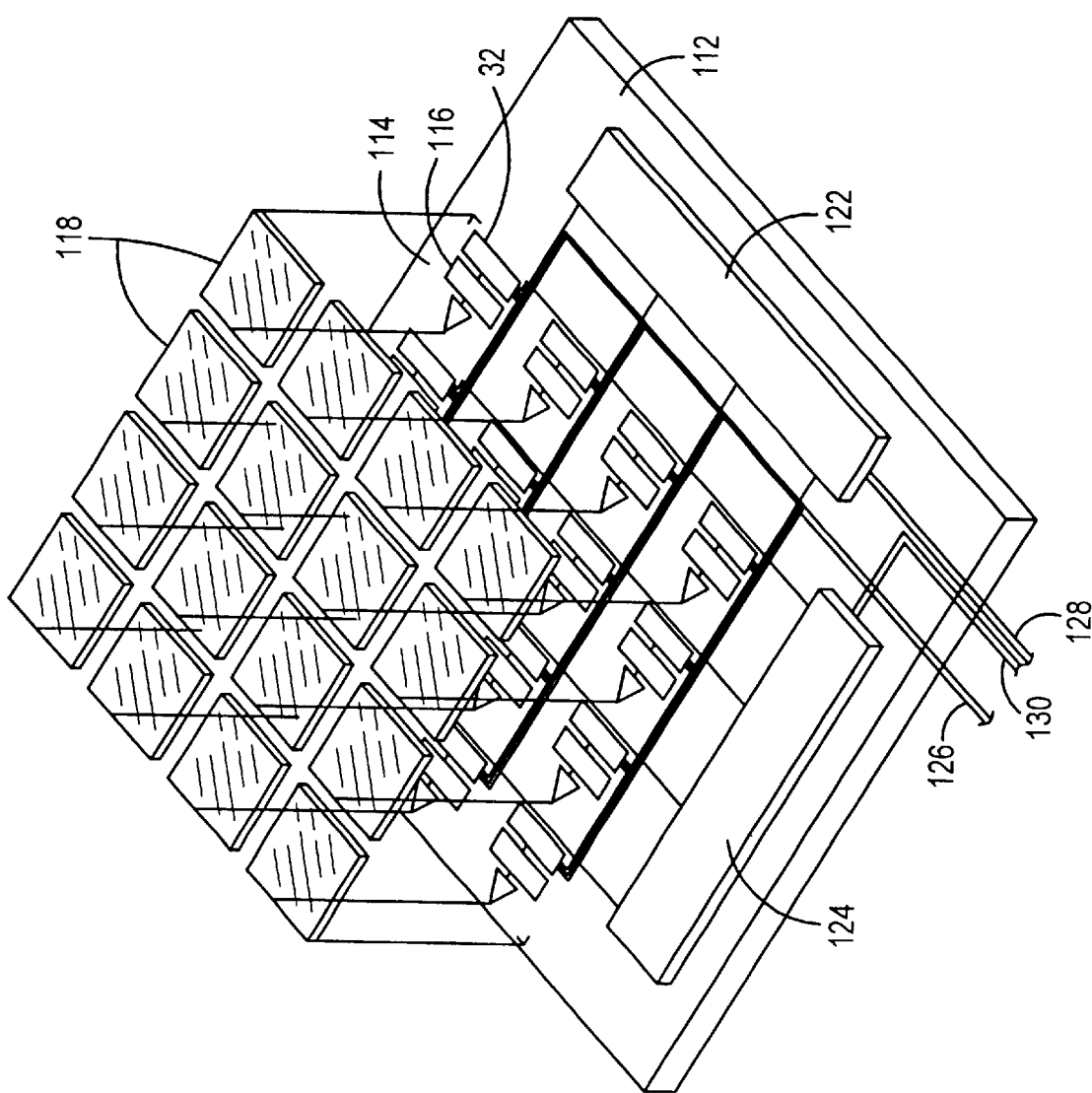
FIG. 10 is a perspective view of a microelectronic array having X-axis and Y-axis address decoders in accordance with the invention.

FIG. 10 is a perspective view of the microelectronic array of FIG. 9 that shows additional features of the array. A semiconductor substrate 112 has a plurality of cells 114 such as RAM cells within the semiconductor substrate 112. A plurality of digital/analog converters 116 is each associated respectively with a cell 114. Each digital/analog converter 116 is respectively electrically coupled to an electrode 118, which is supported by semiconductor substrate 112. The electrical coupling is achieved by means of, for example, conventional inter-layer metallic "vias." FIG. 10 depicts optional buffer amplifier 120, which functions to isolate the digital analog converters from electrical loads applied to their electrodes. Address decoders 122 and 124 are in communication with each of cells 114 by means of, for example, conductive metallization interconnection paths. Data bus 126 is in communication with each of cells 114 by similar means. The data bus 126 delivers numerical data to each of cells 114. Also included are address buses 128 and 130, which deliver addresses to address decoders 122 and 124, respectively, and are in communication therewith by means similar to that described above for the address decoders and the data bus.

Each of cells 114 comprises storage means 132 for storing numerical data. Storage means 132 is in communication with a digital/analog converter 116 in each cell 114 by means similar to that mentioned above. Storage means 132 may be similar to that known in the art as, for example, D-type static flip-fops, a latch, a capacitor storing an analog value, and the like. The storage means may be a dynamic RAM replicator latch with a capacitor, which can store data but needs to be refreshed.

The storage means may store a value representative of a voltage or merely the fact that a cell was selected and the electrode is more or less switched to an analog bus. Both situations are exemplified by D-type flip-flops in conjunction with a digital bus.

In a preferred embodiment, data such as numerical data is sent to storage means 132 of each of cells 114 by means of the data bus. The numerical data is representative of an electric signal as explained in more detail below. Addresses are sent to address decoders 122 and 124 whereby the numerical data is stored in the storage means and electric signals are selectively applied to each of the electrodes by means of digital/analog converters 116. A reaction takes place proximal to and in response to the field at the electrodes.

The numerical data may be, for example, binary numerical data; in a simple case representative of values 0 volts and 3 volts, and so forth. In the latter case, the data is represented by a single bit, 0 or 1 ("0"→0 volts and "1"→3 volts).

Figure 11:
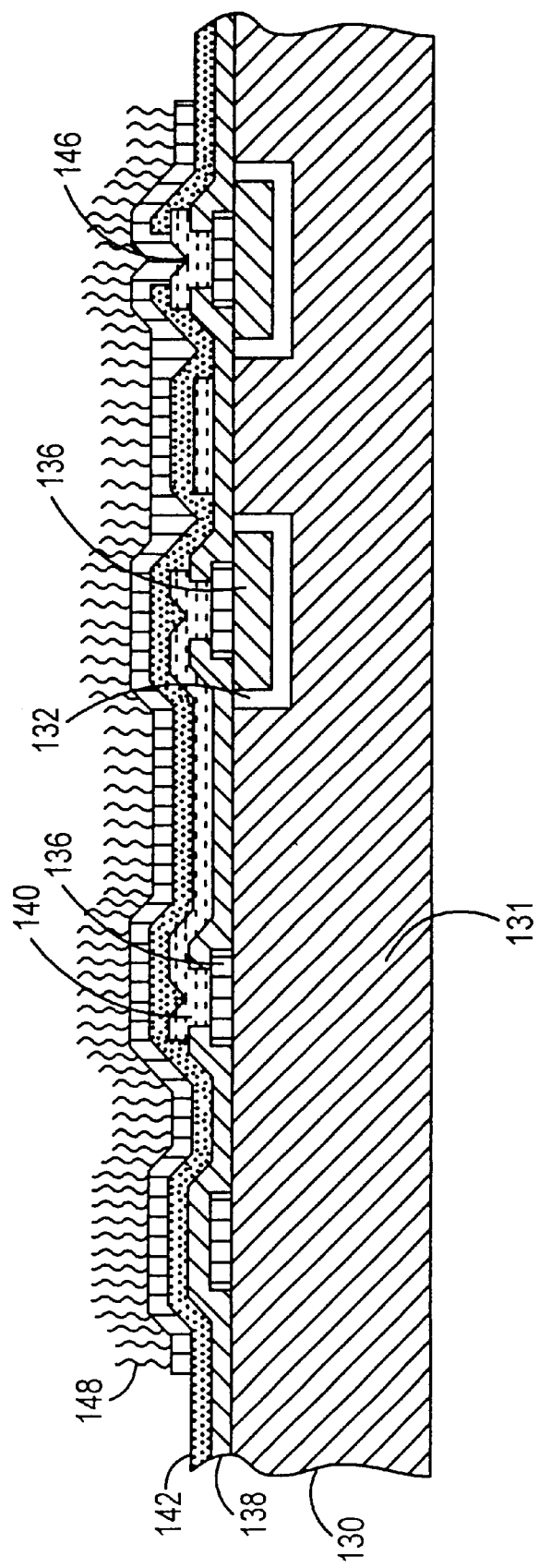
FIG. 11 is a cross-section view of the microelectronic array of FIGS. 9 and 10.

FIG. 11 depicts, in cross-section, a portion of a device in accordance with the present invention showing an electrode assembly. P-substrate 131 contains depletion regions 132 and N-diffusion regions 134. Metal layer 136 is formed from a metal and is found within insulator layer 138. Above metal layer 136 lies metal layer 140, which is found within insulator layer 142. The uppermost layer 144 is also formed from a metal and is the outer layer of the electrode and has oligonucleotides 148 attached thereto. Via 146 is formed by the interconnection of layers 136, 140, and 144, which may be referred to as metallization layers. In some systems, it may be desirable that the surface of the electrode be flat. In this circumstance, the circuitry may be fabricated so as to lie between the electrodes and not underlying them as shown in FIG. 11.

Gold may be employed for one or more metallization layers. For cost reasons, in the present invention aluminum is preferred for the intermediate metal layers and gold for the top layer, which would be the electrodes. Fixed electrodes may be plated over by processes well-known in the art of IC fabrication, with a variety of metals, including gold and nickel, chosen to be the most compatible with the oligomer primer attachment chemistry. In addition to aluminum, suitable metals for circuitry include gold, tin, platinum, palladium, and various metal combinations.

The insulator layers 138 are usually made of an insulating material, i.e., a non-conductive material such as silicon dioxide and the like. The insulator layers are grown above and intrinsically adhered to the metal layers. The overcoat layer is conveniently applied by deposition techniques, e.g., plasma enhanced chemical vapor deposition, and the like.

The connections between the electrodes and the circuit cells are provided by the interconnected layers of metal and insulator by means of holes in the insulator. See, for example, the depiction of via 146 in FIG. 11. These holes are typically on the order of fractions of microns, usually about 0.2 to about 2 microns, in diameter and may be formed of microlithographic or other techniques well-known in the art of IC fabrication such as electron beam lithography, ion beam lithography, or molecular beam epitaxy.

The electrodes may be either left exposed or, alternatively, they may be overcoated with an insulator such as $SiO_2$. In the former case, with an aqueous conductive analysis environment, current flow will take place together with electrochemical reactions. Either the exposed electrodes or $SiO_2$ overcoated electrodes are amenable to an organic non-conductive chemistry in which mobility is effected by the action of a simple electrostatic field. Such coatings may also be important for attaching or synthesizing binding sites (DNA probes) for the specific DNA targets of interest.

The operation of the microelectronic array chip is best understood by considering the case where the chips are processed individually. Referring now to FIG. 10, less than 20 electrical connections to the chip are required for a 16,384-element embodiment. Fourteen lines are required for address, 2 for data, and a few more for power and ground. The 14 address lines carry logic signals representing $2,614$ or 16,384 states. Since the array is most advantageously made square, 7 lines are dedicated to encoding the X-address and 7 lines are dedicated to encoding the Y-address. These 7 lines are fed each to the X-address decoder and the Y-address decoder.

The 7 lines connected to each decoder can represent $2^7$ or 128 states. The output of each decoder is 128 lines. Only one output line is active at a time, namely, the one representing the state of the 7 address lines. For example, a 14-bit address sent to the chip with value of 00000000000010 has a decimal value of 2. Splitting the address into two 7-bit bytes, an address of 0000010 would be sent to the X-axis decoder and an address of 0000000 would be sent to the Y-axis decoder. The 0000000 sent to the Y-axis decoder causes the first or lowest of its 128 output lines to become active. Accordingly, the line might be set "high," while the remaining 127 lines would be set "low," which means that the line is set to a voltage of zero. The 0000010 address, a binary "2," is the third ascending state that can be represented and, thus, causes the third line of the X-axis decoder to be set active (or "high"). In this way, a positive ion such as a nucleotide phosphoramidite is attracted to the electrode governed by this cell.

FIG. 10 may be visualized as representing the lower-leftmost 16-element corner of the 16,384-element array. The nearest element has address 00000000000000; the rightmost, 00000000000011; the leftmost, 00000110000000; and the uppermost, 00000110000011.

The 128 decoded address lines from each decoder form a grid on the chip. At each intersection is a cell of circuitry and an electrode. Each cell is only addressed when both the X and Y decoded address lines are active. Thus, for any applied 14-bit address, only one cell is addressed at a time.

In this embodiment, two data lines enter the chip. They are capable of representing $2^2$ or 4 logic states. These will ultimately produce one of four possible voltages on whichever electrode in the array happens to be addressed. More specifically, when a circuit cell is addressed, it latches the data from the data lines by means of two D-type flip-flops. This data is held, or latched, while the process proceeds to latch independent data into each of the other 16,383 cells. The state latched into each circuit cell may have a value of 00, 01, 10 or 11. The latching is static, as opposed to dynamic, for simplicity. The operation is reminiscent of the behavior of computer random access memory (RAM) chips. The preferred mode of operation is as a static RAM, which means that data does not need to be periodically refreshed by read/write cycles. However, this is not a requirement. The byte length is 2 bits.

The state latched into each circuit cell is delivered to a digital-to-analog converter (DAC) for conversion to an analog voltage (for example, 0, 1, 2, or 3 volts). This output is shown buffered by a unity-gain amplifier. However, drive requirements for the electrode are so small that the amplifier may be incorporated as a functional part of the DAC itself and, in that sense, eliminated.

A beneficial feature not shown in FIG. 10 is means to electrically test the device before the chemical cycles commence. This is easily accomplished by adding an additional line exiting the chip, which is connected in parallel to every array circuit cell. Each cell has an analog switch, which allows sequential connecting of its analog output voltages to the bus when the cell is addressed. The test and verification cycle is as follows: Each cell is written to four times, once with each of its four allowable 00, 01, 10 and 11 states. After each write, the analog bus is monitored for presence of the correct voltage.

The size of the array may be varied depending on the application as discussed above. Fewer or more elements may be employed, depending on cost considerations, the size of the sample available for analysis and the size of the electrodes necessary to obtain the required sensitivity.

Greater or fewer voltage states may be provided for on each electrode as well as voltages of both polarities. In this regard, the voltages may be from any value between the two positive and negative extremes of supply voltages available to the chip. The particular voltages selected will depend on the application in which the device is used. The voltage range does not need to be represented in equal steps; for example, four binary states could be assigned values of 0, 0.5, 4.5, and 5.0 volts.

In its simplest form, only two voltage levels are provided. In this approach, most of the complexity of the cell vanishes and a 1-bit latch is all that is required. In this form, the density of an array can be increased considerably.

The spacing between sites on the device is determined by the ease of fabrication, the requirement for resolution between the various sites, and the number of sites desired on a device. However, particular spacing between sites or special arrangement or geometry of the sites is not necessary for device function. Any combination of microlocations (i.e., underlying electrodes) can operate over the complete device area. Nor is it necessary to enclose the device or confine the sites with dielectric boundaries. The device functions by attaching molecules such as specific binding molecules, chemical and analytical reagents to the surface of an addressable site adjacent an electric field that is selectively generated.

All principles described herein can be applied to arrays other than DNA arrays. Specifically, any array of target binding sites and targets for which ECL readout could be generated is applicable. For example, target binding site and target combinations can include receptor/ligand, ligand/receptor, antigen/antibody, hapten/antibody, antibody/hapten, and antibody/antigen.

What is claimed is:

1. A method for reading data from microlocations of a microelectronic array comprising steps of:

providing said microelectronic array having a plurality of individually activatable microlocations, each microlocation having molecular biological material thereon;

selecting a biological detection technique by which optical energy is generated in response to applying activation energy to a microlocation at which molecular biological material resides, with a specific characteristic of the generated optical energy being related to a specific characteristic of said molecular biological material;

simultaneously activating a plurality of microlocations such that each activated microlocation is surrounded by a plurality of inactive microlocations, said plurality of microlocations being activated to generate optical energy at each activated microlocation having molecular biological material, said optical energy being indicative of said specific attribute of molecular biological material at each microlocation, said surrounding inactive microlocations serving to reduce optical interference between said plurality of activated microlocations;

simultaneously detecting said optical energy generated at each said activated microlocation; and quantifying said specific attribute for said molecular biological material residing at each of said activated microlocations based upon said detected optical energy at each said activated microlocation.

2. The method of claim 1 wherein said selected biological detection technique utilizes electrochemiluminescence to generate said optical energy, said specific characteristic of said generated optical energy being intensity and said specific characteristic being a concentration of said molecular biological material.

3. The method of claim 2 wherein said step of activating includes a step of simultaneously applying a voltage to a plurality of electrodes having an arrangement that corresponds with an arrangement of said plurality of microlocations.

4. The method of claim 1 wherein said step of activating includes a step of activating microlocations at the intersections of every $M^{th}$ column and every $N^{th}$ row, where M and N are integers greater than 1.

5. A method for reading out data from electronically addressable microlocations of a microelectronic array comprising the steps of:

providing said microelectronic array having a plurality of individually activatable microlocations, each microlocation having molecular biological material thereon;

utilizing electrochemiluminescence to generate optical energy in response to electrical energy applied to a plurality of discrete microlocations to detect molecular biological material at said discrete microlocations;

simultaneously activating a plurality of microlocations of said microelectronic array such that each activated microlocation is surrounded by a plurality of inactive microlocations, said plurality of microlocations being activated in order to generate optical energy at each activated microlocation, where the optical energy is related to a concentration of molecular biological material at each activated microlocation;

simultaneously detecting generated optical energy from each activated microlocation with a multi-dimension resolving detector; and determining a concentration of molecular biological material at each activated microlocation, where said determined concentration is related to said detected optical energy at respective microlocations.

6. The method of claim 5 wherein said step of simultaneously activating a plurality of microlocations includes a step of simultaneously activating microlocations at the intersections of every $M^{th}$ column of microlocations and every $N^{th}$ row of microlocations in said microelectronic array, where M and N are integers greater than 1.

7. The method of claim 6 wherein said step of simultaneously activating includes a step of utilizing on-chip address decoders to simultaneously activate said plurality of microlocations.

8. The method of claim 4 further including a step of changing said activated columns and rows such that previously inactive microlocations are activated.

9. A method for reading data from microlocations of a microelectronic array comprising steps of:

providing said microelectronic array having a plurality of individually activatable microlocations, each microlocation having molecular biological material thereon;

selecting a biological detection technique by which optical energy is generated in response to applying activation energy to a microlocation at which molecular biological material resides, with a specific characteristic of the generated optical energy being related to a specific characteristic of said molecular biological material;

activating a plurality of columns of microlocations simultaneously to generate optical energy at each microlocation having molecular biological material, each of said activated columns being separated by at least one column of inactive microlocations, said optical energy being indicative of said specific attribute of molecular biological material at each microlocation;

simultaneously detecting said optical energy generated at each said activated microlocation; and quantifying said specific attribute for said molecular biological material residing at each of said activated microlocations based upon said detected optical energy at each said activated microlocation.

10. The method of claim 9 wherein said step of activating includes activating every $M^{th}$ column of microlocations, where M is an integer that is greater than 1.

11. The method of claim 10 wherein M is equal to 2, such that every other column of microlocations is activated in parallel.

12. The method of claim 10 further including a step of changing said activated columns by one column, such that previously inactive columns of microlocations are activated.

13. A method for reading data from microlocations of a microelectronic array comprising steps of:

providing said microelectronic array having a plurality of individually activatable microlocations, each microlocation having molecular biological material thereon;

selecting a biological detection technique by which optical energy is generated in response to applying activation energy to a microlocation at which molecular biological material resides, with a specific characteristic of the generated optical energy being related to a specific characteristic of said molecular biological material;

activating a plurality of rows of microlocations simultaneously to generate optical energy at each microlocation having molecular biological material, each of said activated rows being separated by at least one row of inactive microlocations, said optical energy being indicative of said specific attribute of molecular biological material at each microlocation, N being an integer that is greater than 1;

simultaneously detecting said optical energy generated at each said activated microlocation; and quantifying said specific attribute for said molecular biological material residing at each of said activated microlocations based upon said detected optical energy at each said activated microlocation.

14. The method of claim 13 wherein said step of activating includes activating every $N^{th}$ row of microlocations, where N is an integer greater than 1.

15. The method of claim 14 wherein N is equal to 2, such that every other row of microlocations is activated in parallel.

16. The method of claim 14 further including a step of changing said activated rows by one row, such that previously inactive rows of microlocations are activated.

17. A method for reading data from microlocations of a microelectronic array comprising steps of:

providing said microelectronic array having a plurality of individually activatable microlocations, each microlocation having molecular biological material thereon;

selecting a biological detection technique by which optical energy is generated in response to applying activation energy to a microlocation at which molecular biological material resides, with a specific characteristic of the generated optical energy being related to a specific characteristic of said molecular biological material;

simultaneously activating microlocations at the intersections of every $M^{th}$ column and every $N^{th}$ row to generate optical energy at each microlocation having molecular biological material, said optical energy being indicative of said specific attribute of molecular biological material at each microlocation, M and N being integers greater than 1;

simultaneously detecting said optical energy generated at each said activated microlocation; and quantifying said specific attribute for said molecular biological material residing at each of said activated microlocations based upon said detected optical energy at each said activated microlocation.

18. The method of claim 17 further including a step of changing said activated columns and rows such that previously inactive microlocations are activated.

19. A method for reading out data from electronically addressable microlocations of a microelectronic array comprising the steps of:

utilizing electrochemiluminescence to generate optical energy in response to electrical energy applied at a discrete microlocation to detect molecular biological material at said discrete microlocation;

simultaneously activating microlocations at the intersections of every $M^{th}$ column of microlocations and every $N^{th}$ row of microlocations in said microelectronic array in order to generate optical energy at each activated microlocation, where the optical energy is related to a concentration of molecular biological material at each activated microlocation, M and N being integers greater than 1;

simultaneously detecting generated optical energy from each activated microlocation with a multi-dimension resolving detector; and determining a concentration of molecular biological material at each activated microlocation, where said determined concentration is related to said detected optical energy at respective microlocations.

* * * * *